US008895066B2

(12) United States Patent
Bichara et al.

(10) Patent No.: US 8,895,066 B2
(45) Date of Patent: Nov. 25, 2014

(54) BILAYER COMPOSITION FOR THE SUSTAINED RELEASE OF ACETAMINOPHEN AND TRAMADOL

(75) Inventors: Ali Bichara, Montreal (CA); Sonia Gervais, Laval (CA); Dorothee Le Garrec, Montreal (CA); Patricia Ouadji, Laval (CA); Vinayak Sant, Montreal (CA); Shiva Gosein, LaSalle (CA); Vincent Lemaire, Montreal (CA); Samir Taga, Montreal (CA); Damon Smith, Saint-Laurent (CA)

(73) Assignees: Paladin Labs Inc., Montreal (CA); Paladin Labs Europe Limited, Dublin (IE); Paladin Labs (Barbados) Inc., Hastings (BB)

( * ) Notice: Subject to any disclaimer, the term of this patent is extended or adjusted under 35 U.S.C. 154(b) by 855 days.

(21) Appl. No.: 12/252,117

(22) Filed: Oct. 15, 2008

(65) Prior Publication Data
US 2009/0130183 A1 May 21, 2009

Related U.S. Application Data

(60) Provisional application No. 60/980,203, filed on Oct. 16, 2007.

(51) Int. Cl.
| *A61P 25/04* | (2006.01) |
| *A61K 31/167* | (2006.01) |
| *A61K 9/70* | (2006.01) |
| *A61K 31/137* | (2006.01) |
| *A61K 31/00* | (2006.01) |
| *A61K 9/20* | (2006.01) |

(52) U.S. Cl.
CPC ............ *A61K 9/2072* (2013.01); *A61K 31/167* (2013.01); *A61K 31/137* (2013.01); *A61K 31/00* (2013.01); *A61K 9/2077* (2013.01); *A61K 9/2086* (2013.01)
USPC ........................... 424/474; 424/443; 514/630

(58) Field of Classification Search
USPC ....................................................... 424/472
See application file for complete search history.

(56) References Cited

U.S. PATENT DOCUMENTS

| 3,652,589 | A | 3/1972 | Flick et al. |
| 4,820,522 | A | 4/1989 | Radebaugh et al. |
| 4,968,509 | A | 11/1990 | Radebaugh et al. |
| 5,004,613 | A | 4/1991 | Radebaugh et al. |
| 5,133,974 | A | 7/1992 | Paradissis et al. |
| 5,336,691 | A * | 8/1994 | Raffa et al. ............... 514/629 |
| 5,456,921 | A | 10/1995 | Mateescu et al. |
| 5,478,577 | A | 12/1995 | Sackler et al. |
| 5,591,452 | A | 1/1997 | Miller et al. |
| 5,601,842 | A | 2/1997 | Bartholomaeus |
| 5,603,956 | A | 2/1997 | Mateescu et al. |
| 5,616,343 | A | 4/1997 | Cartilier et al. |
| 5,672,360 | A | 9/1997 | Sackler et al. |
| 5,681,583 | A | 10/1997 | Conte et al. |
| 5,773,031 | A | 6/1998 | Shah et al. |
| 5,807,575 | A | 9/1998 | Dumoulin et al. |
| 6,103,261 | A | 8/2000 | Chasin et al. |
| 6,156,342 | A | 12/2000 | Sriwongjanya et al. |
| 6,194,000 | B1 | 2/2001 | Smith et al. |
| 6,197,336 | B1 * | 3/2001 | Grassano et al. ............ 424/464 |
| 6,210,714 | B1 | 4/2001 | Oshlack et al. |
| 6,245,357 | B1 | 6/2001 | Edgren et al. |
| 6,245,387 | B1 | 6/2001 | Hayden |
| 6,254,887 | B1 | 7/2001 | Miller et al. |
| 6,284,273 | B1 | 9/2001 | Lenaerts et al. |
| 6,326,027 | B1 | 12/2001 | Miller et al. |
| 6,372,255 | B1 | 4/2002 | Saslawski et al. |
| 6,387,404 | B2 | 5/2002 | Oshlack et al. |
| 6,399,096 | B1 | 6/2002 | Miller et al. |
| 6,419,957 | B1 | 7/2002 | Lenaerts et al. |
| 6,607,748 | B1 | 8/2003 | Lenaerts et al. |
| 6,667,060 | B1 | 12/2003 | Vandecruys et al. |
| 6,761,895 | B2 | 7/2004 | Sawada et al. |
| 6,968,551 | B2 | 11/2005 | Hediger et al. |
| RE39,221 | E | 8/2006 | Raffa et al. |
| 7,083,807 | B2 | 8/2006 | Fanara et al. |
| 7,374,781 | B2 | 5/2008 | Zhang et al. |
| 2002/0106408 | A1 * | 8/2002 | Bacon et al. ............ 424/471 |
| 2003/0092724 | A1 | 5/2003 | Kao et al. |
| 2004/0013726 | A1 * | 1/2004 | Lenaerts et al. ............ 424/465 |
| 2004/0131671 | A1 | 7/2004 | Zhang et al. |
| 2004/0202716 | A1 | 10/2004 | Chan et al. |

(Continued)

FOREIGN PATENT DOCUMENTS

| CA | 2414349 A1 | 1/2002 |
| EP | 0 566 709 | 10/1993 |

(Continued)

OTHER PUBLICATIONS

Schug, Stephan A. "Combination analgesia in 2005—a rational approach: focus on paracetamol-tramadol", Clin. Rheumatol (2006) 25 (Suppl1): S16-S21. Published online Jun. 2, 2006.*

(Continued)

*Primary Examiner* — Audrea Buckley
(74) *Attorney, Agent, or Firm* — Goodwin Procter LLP

(57) ABSTRACT

The invention relates to a bilayer composition for the delivery of acetaminophen and tramadol over at least a twelve hour period following initial administration. A single administration of the bilayer composition can provide analgesia starting in less than half an hour to about one hour after initial administration with a duration of at least twelve hours after initial administration.

20 Claims, 8 Drawing Sheets

(56) References Cited

U.S. PATENT DOCUMENTS

| | | | |
|---|---|---|---|
| 2005/0112195 A1 | 5/2005 | Cruz et al. | |
| 2005/0157382 A1 | 7/2005 | Kafka et al. | |
| 2005/0276852 A1 | 12/2005 | Davis et al. | |
| 2006/0165777 A1* | 7/2006 | Solomon et al. | 424/451 |
| 2006/0172006 A1* | 8/2006 | Lenaerts et al. | 424/468 |
| 2006/0204578 A1* | 9/2006 | Vergez et al. | 424/473 |
| 2006/0240107 A1 | 10/2006 | Lenaerts et al. | |
| 2006/0257473 A1 | 11/2006 | Puranajoti | |
| 2007/0003618 A1 | 1/2007 | Lenaerts et al. | |
| 2007/0048376 A1 | 3/2007 | Baichwal et al. | |
| 2007/0128269 A1 | 6/2007 | Gervais et al. | |
| 2007/0207200 A1 | 9/2007 | Plachetka et al. | |
| 2007/0237816 A1 | 10/2007 | Finkelstein | |
| 2007/0281018 A1 | 12/2007 | Qiu et al. | |
| 2008/0031901 A1 | 2/2008 | Qiu et al. | |
| 2009/0047345 A9 | 2/2009 | Lenaerts et al. | |
| 2011/0166171 A1 | 7/2011 | Qiu et al. | |

FOREIGN PATENT DOCUMENTS

| | | |
|---|---|---|
| WO | WO-93/04675 A1 | 3/1993 |
| WO | WO-01/45676 | 6/2001 |
| WO | WO-01/80834 A1 | 11/2001 |
| WO | WO-02/28383 A1 | 4/2002 |
| WO | WO-2004/006904 | 1/2004 |
| WO | WO-2004/038428 A2 | 5/2004 |

OTHER PUBLICATIONS

Medve et al. (2001) "Tramadol and Acetaminophen Tablets for Dental Pain," Anesth. Prog. 48:79-81.

Desmeules et al. "Clinical pharmacology and rationale of analgesic combinations" Eur J. Anaesthesiol. 2003; 20 Suppl 28 7-11.

Edwards et al. Combination analgesic efficacy: individual patient data meta-analysis of single-dose oral tramadol plus acetaminophen in acute postoperative pain. J. Pain Symptom. Manage. 2002; 23(2) 121-130.

Fricke et al. A Double-blind, single-dose comparison of the analgesic efficacy of tramadol/acetaminophen combination tablets, hydrocodone/acetaminophen combination tablets, and placebo after oral surgery. Clin. Ther. 2002; 24(6): 953-968.

Hiller et al. "Ultracet: a new combination analgesic" J. Mass Dent. Soc. 2003; 52(2): 38-40.

Lee "Clinical Pharmacology and Biopharmaceutics Review(s) of Application No. 21-123 by the FDA Center for Drug Evaluation and Research" Mar. 2000.

Lee et al. "Medical Review of Application No. 21-123 by the FDA Center for Drug Evaluation and Research" Apr. 30, 2000.

McClellan et al. "Tramadol/paracetamol." Drugs 2003; 63(11) 1079-1086.

McNeil's background package on acetaminophen for the Sep. 19, 2002 Nonprescription Drugs Advisory Committee Meeting—announced in the Federal Register of Aug. 20, 2002.

Mateescu "Use of reticulated amylose for the quantitative determination of alpha- and beta-amylase present in an amylolytic preparation" Biochemie 1978; 60(5):535-7.

Raffa "Pharmacology of oral combination analgesics: rational therapy for pain" J. Clin. Pharm and Therap. 2001; 26, 257-264.

Tallarida et al. "Testing for synergism over a range of fixed ratio drug combinations: replacing the isolbologram" Life Sci. 1996; 58(2): PL23-28.

Smith et al. (2004) "Combination tramadol plus acetaminophen for postsurgical pain," The American Journal of Surgery 187(4):521-527.

Extended European Search Report for European Patent Application No. EP 08839570.2, mailed Jun. 6, 2012.

* cited by examiner

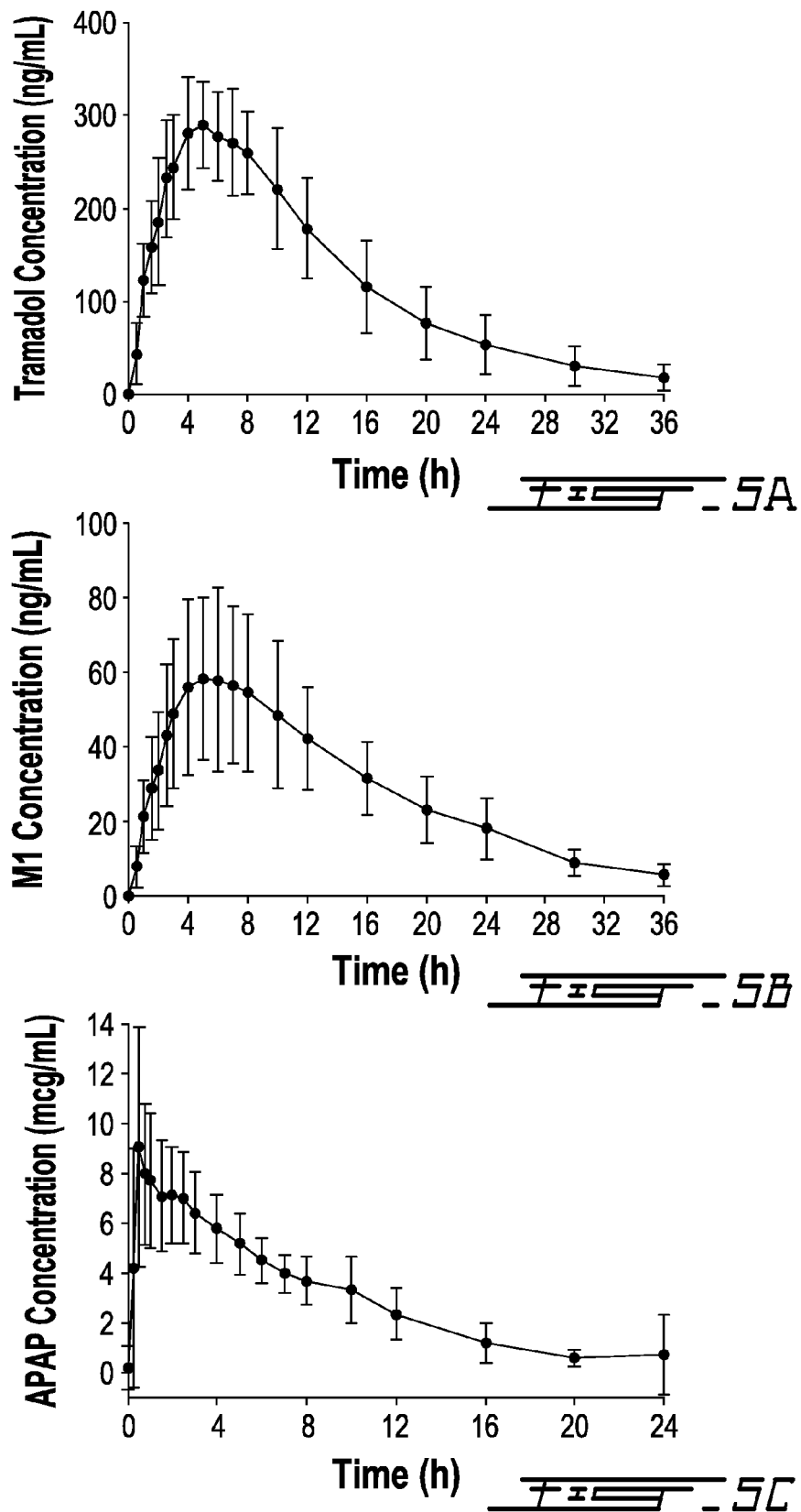

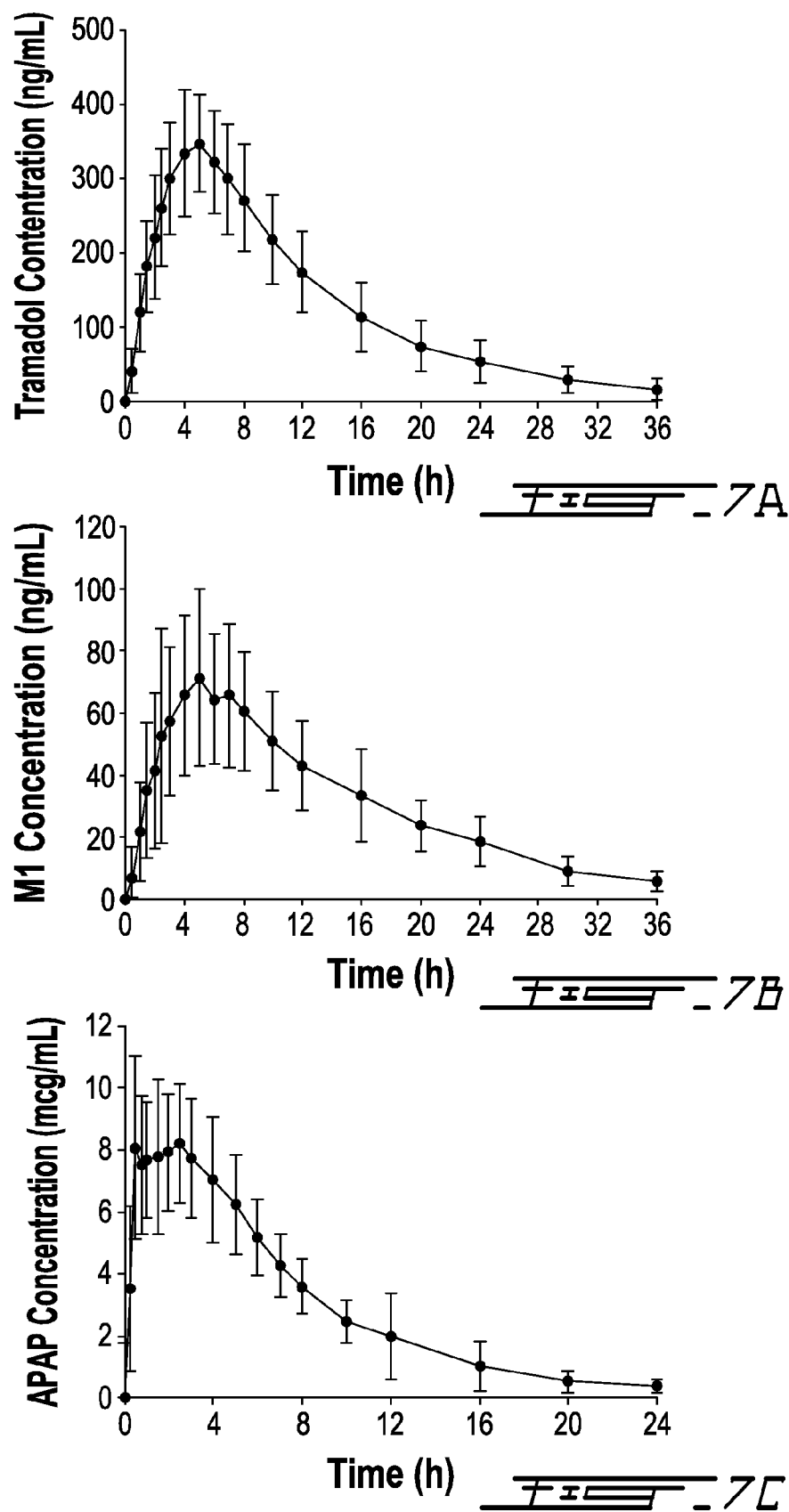

BILAYER COMPOSITION FOR THE SUSTAINED RELEASE OF ACETAMINOPHEN AND TRAMADOL

REFERENCE TO RELATED APPLICATIONS

This application claims the benefit of and priority to U.S. Patent Application Ser. No. 60/980,203, filed Oct. 16, 2007, the entire disclosure of which is incorporated by reference herein.

FIELD OF THE INVENTION

The invention relates generally to tramadol and acetaminophen containing compositions, and more particularly to a bilayer composition for the controlled release tramadol and acetaminophen.

BACKGROUND

Acetaminophen and tramadol are commonly used analgesics, and have been used alone or in combination for a number of years. An immediate release tablet composition comprising tramadol and acetaminophen, and its use, has been described, for example, in U.S. Pat. No. 5,336,691, which reissued as U.S. Pat. No. RE39,221. Immediate release compositions have been available commercially under the tradename Ultracet®, which usually are administered in adults every four to six hours. Ultracet® has been used successfully in acute pain management for many years.

Nevertheless, there is a desire to produce sustained release formulations containing both tramadol and acetaminophen to facilitate better pain management and patient convenience and quality of life. It is contemplated that sustained release products will provide improved patient convenience as they would not require remembering to take, and then taking, as many doses over a twelve hour period. This feature has the added benefit of avoiding break-through pain which may occur if a repeat dose of an immediate release product is omitted or mis-timed. Furthermore, it is believed that sustained release products will improve quality of life since they generally reduce fluctuations in plasma concentrations, potentially providing more consistent analgesia.

In general, because Acetaminophen is a low potency drug requiring large doses to be administered for effective and prolonged analgesia and because the distal regions of the gastrointestinal tract such as the colon have a small surface area for absorption as compared to the proximal small bowel, it is believed that it is difficult to administer acetaminophen in a single dosage to achieve sufficiently high plasma concentrations to achieve sustained analgesia for more than eight hours. A number of sustained release formulations for the delivery of a combination of acetaminophen and tramadol have been described, for example, in U.S. Pat. No. 7,374,781 and U.S. Patent Publication No. US2003/0092724 A1. No sustained release formulations containing both tramadol and acetaminophen, however, have been approved to date in the U.S. or Europe.

As a result, there is still a need for compositions that permit the delivery of acetaminophen and tramadol over prolonged periods of time, for example, at least about twelve hours, to facilitate pain management over that period of time.

SUMMARY OF THE INVENTION

The invention provides a bilayer composition for the delivery of tramadol and acetaminophen over at least twelve hours following administration. Administration of such a composition provides a rapid onset of analgesia, for example, in about half an hour to about one hour after administration, and a duration of analgesia lasting at least about twelve hours after administration. It is contemplated that the compositions release the acetaminophen and tramadol so that both active ingredients are capable of acting synergistically with one another in vivo to provide pain relief over a twelve hour period of time.

In one aspect, the invention provides a bilayer composition for the release of acetaminophen and tramadol. The bilayer composition comprises a first layer defining a rapid-release portion that comprises acetaminophen. The bilayer composition also comprises a second layer adjacent the first layer defining a sustained release portion that comprises acetaminophen and tramadol as active ingredients, and cross-linked high amylose starch as a controlled release excipient. The compositions have in vitro release kinetics such that, when tested in a U.S.P. Type III Apparatus at 20 dips per minute at 37° C. in a solution of 250 mL of potassium phosphate monobasic pH 6.8 for one hour, after which the solution is removed and replaced with a fresh 250 mL of potassium phosphate monobasic pH 6.8 for eleven hours, the acetaminophen and tramadol are released with kinetics set forth in TABLE 1.

TABLE 1

| Time (hours) | Acetaminophen % release (by weight) | Tramadol % release (by weight) |
| --- | --- | --- |
| 1 | 30-60 | ≤35 |
| 4 | 60-90 | 45-65 |
| 8 | 80-90 | ≤90 |
| 12 | ≥90 | ≥90 |

In one embodiment, the first layer comprises from about 70% to about 90% w/w of acetaminophen, whereas the second layer comprises, from about 40% to about 60% w/w of acetaminophen and from about 5% to about 15% w/w of tramadol.

In another aspect, the invention provides a bilayer composition for the delivery of tramadol and acetaminophen. The bilayer composition comprises a first layer defining a rapid release portion of the composition that comprises acetaminophen. The bilayer composition comprises a second layer defining a sustained release portion of the composition that comprises acetaminophen, tramadol, and cross-linked high amylose starch. The bilayer composition, when administered to a mammal (for example, a human), releases the acetaminophen and the tramadol so that the ratio by weight of acetaminophen:tramadol in the plasma of the mammal is at least 6:1 for at least 12 hours following initial administration to the mammal.

The bilayer compositions of the invention, when administered to a mammal, for example, a human, as a single bolus dose can produce analgesia within about one half hour to about one hour after ingestion that lasts for at least twelve hours after ingestion. Accordingly, the compositions of the invention can be used to provide both rapid and sustained analgesic relief to a patient in need thereof.

BRIEF DESCRIPTION OF THE DRAWINGS

The invention is illustrated but is not limited by the annexed drawings, in which

FIGS. 5A-5C are graphs illustrating the in vivo mean plasma concentrations (+SD) of tramadol (FIG. 5A), O-desmethyltramadol (M1)(FIG. 5B), and acetaminophen (APAP) (FIG. 5C) following a single, two-tablet dose of Composition 1 (each tablet containing 75 mg tramadol and 650 mg of acetaminophen) under fasting conditions;

FIGS. 7A-7C are graphs illustrating the in vivo mean plasma concentrations (+SD) of tramadol (FIG. 7A), O-desmethyltramadol (M1)(FIG. 7B), and acetaminophen (APAP) (FIG. 7C) following a single, two-tablet dose of Composition 2 (each tablet containing 75 mg tramadol and 650 mg of acetaminophen) under fasting conditions;

DETAILED DESCRIPTION

The invention is based, in part, upon the discovery that it is possible to produce a formulation that permits the independent release of tramadol and acetaminophen from a single dosage form over a twelve hour period of time so as to produce analgesia over the entire twelve hour period. In particular, the formulation is designed to provide a therapeutically effective plasma concentration of acetaminophen starting about half an hour to about one hour after administration, after which the simultaneous release of both tramadol and the residual acetaminophen provide plasma concentrations of each active agent sufficient to achieve analgesic synergy and, therefore, continued effective analgesia over at least twelve hours. Thus, after an initial rapid release of acetaminophen sufficient to bring about the onset of analgesia, the compositions release acetaminophen and tramadol together but at different rates such that they are both capable of achieving intestinal absorption rates and subsequent plasma levels appropriate for synergy in vivo and thereby provide analgesia over a twelve hour period of time. As far as the inventors are aware, it has not been possible to produce until now a formulation in which a single dosage form containing acetaminophen and tramadol achieves the appropriate release and uptake kinetics so as to facilitate rapid but yet sustained analgesia for twelve hours as the dosage form traverses a subject's stomach, upper gastrointestinal tract and lower gastrointestinal tract.

Figure 1:
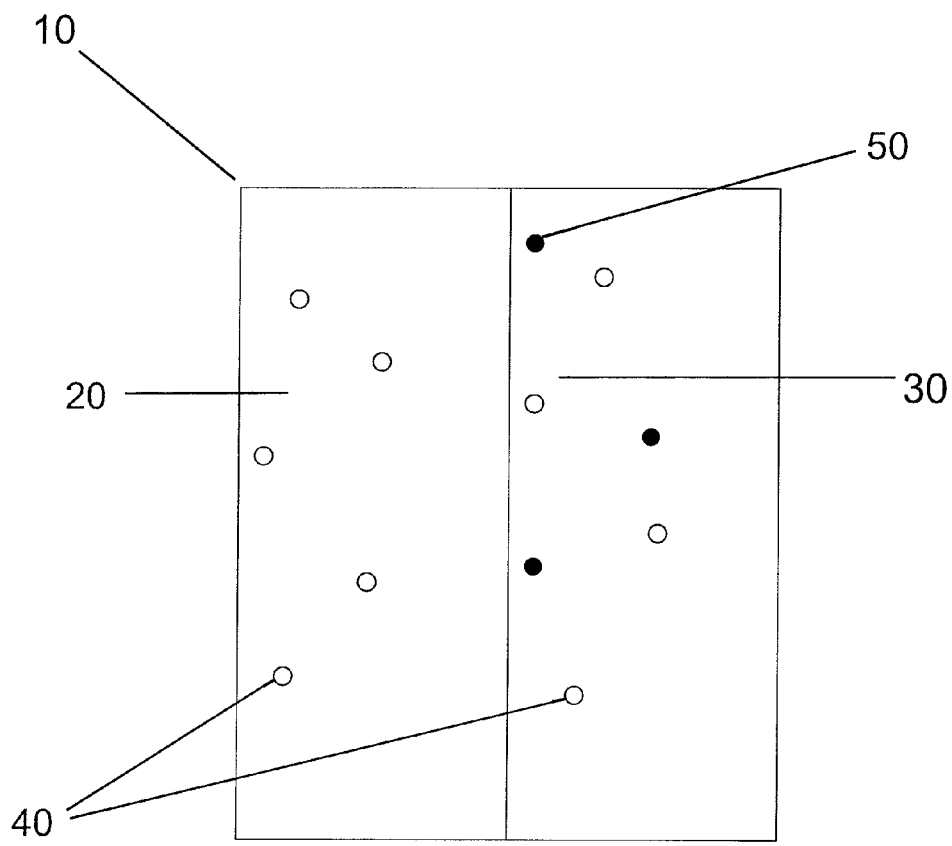
FIG. 1 is a schematic representation of an exemplary bilayer composition of the invention.

FIG. 1 provides a schematic illustration of an exemplary formulation of the invention. In particular, as shown in FIG. 1, bilayer composition 10 comprises a rapid release layer 20 and a sustained release layer 30. Rapid release 20 comprises acetaminophen 40. Sustained release layer 30 comprises both acetaminophen 40 and tramadol 50 in a controlled release excipient, for example, cross-linked high amylose starch. It is understood, however, that for certain formulations, rapid release layer 20 may also include a certain amount of tramadol 50.

In one aspect, the bilayer composition comprises a first layer defining a rapid release portion that comprises acetaminophen. The bilayer composition also comprises a second layer adjacent the first layer defining a sustained release portion that comprises acetaminophen and tramadol as active ingredients, and cross-linked high amylose starch as a controlled release excipient. The compositions have in vitro release kinetics such that, when tested in a U.S.P. Type III Apparatus at 20 dips per minute at 37° C. in a solution of 250 mL of potassium phosphate monobasic pH 6.8 for one hour, after which the initial solution of potassium phosphate is removed and replaced with a fresh 250 mL solution of potassium phosphate monobasic pH 6.8 for another eleven hours, the acetaminophen and tramadol are released with the kinetics set forth in TABLE 1.

The bilayer compositions of the invention contain a first layer defining a rapid release portion (for example, via an immediate release matrix) in which at least 50% (optionally at least 60% or 70%) by weight of the acetaminophen in the rapid release portion is released within 30 minutes when measured in a U.S.P. Type III apparatus under the conditions noted above. Furthermore, the bilayer compositions contain a second layer defining a sustained release portion (for example, via a controlled release matrix) in which no more than 50% (optionally no more than 40% or 30%) by weight of the acetaminophen in the sustained release portion is released within 30 minutes when measured in a U.S.P. Type III apparatus under the conditions noted above. It is understood that the release kinetics can be measured on an intact bilayer tablet, for example, by deconvoluting the release profiles discussed, for example, in Example 1 or by measuring the release of labelled (for example, radiolabelled or fluorescently labelled) acetaminophen. Alternatively, the release kinetics of each layer can be measured separately. For example, the release kinetics can be measured from a composition that contains the same formulation as the rapid release portion and then in a separate experiment from a composition that contains the same formulation as the sustained release portion.

Furthermore, when administered as a single bolus to a mammal, for example, a human, the bilayer composition can achieve (i) a therapeutically effective plasma concentration of acetaminophen starting within about half an hour after initial administration and (ii) combined therapeutically effective plasma concentrations of tramadol and acetaminophen for at least about twelve hours after initial administration.

The term "therapeutic effect" is art-recognized and refers to a local or systemic effect in animals, particularly mammals, and more particularly humans caused by a pharmacologically active substance. The phrase "therapeutically effective amount" means that amount of such a substance that produces some desired local or systemic effect at a reasonable benefit/risk ratio applicable to any treatment. The therapeutically effective amount of such substance will vary depending upon the subject and disease condition being treated, the weight and age of the subject, the severity of the disease condition, the manner of administration and the like, which can readily be determined by one of ordinary skill in the art. For example, certain compositions of the present invention may be administered in sufficient amounts to achieve sufficient plasma concentrations to produce reasonable benefit/risk ratios applicable to such treatment.

In another aspect, the invention provides a bilayer composition for the delivery of tramadol and acetaminophen. The bilayer composition comprises a first layer defining a rapid release portion of the composition that comprises acetaminophen. The bilayer composition comprises a second layer defining a sustained release portion of the composition that comprises acetaminophen, tramadol, and cross-linked high amylose starch. The bilayer composition, when administered to a mammal (for example, a human), releases the acetaminophen and the tramadol so that the ratio by weight of acetaminophen:tramadol in the plasma of the mammal is greater than 5.7:1, preferably at least 6:1 for at least 12 hours following initial administration to the mammal.

Figure 4:
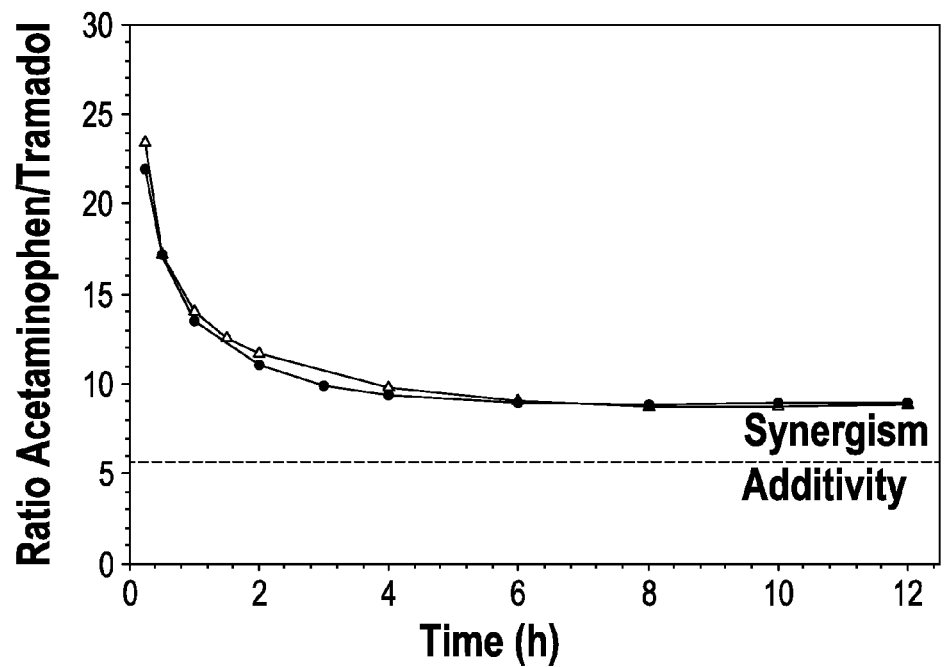
FIG. 4 is a graph showing the ratio of acetaminophen to tramadol released from Composition 1 of Example 1 (-Δ-) or Composition 2 of Example 2 (-●-) as a function of time in a U.S.P. Type III apparatus. The dashed line illustrates the ratio of acetaminophen to tramadol (about 5.7:1 based on preclinical studies), above which, the effects of the active ingredients are believed to be synergistic and, below which, the effects of the active ingredients are believed to be additive.
Figure 9:
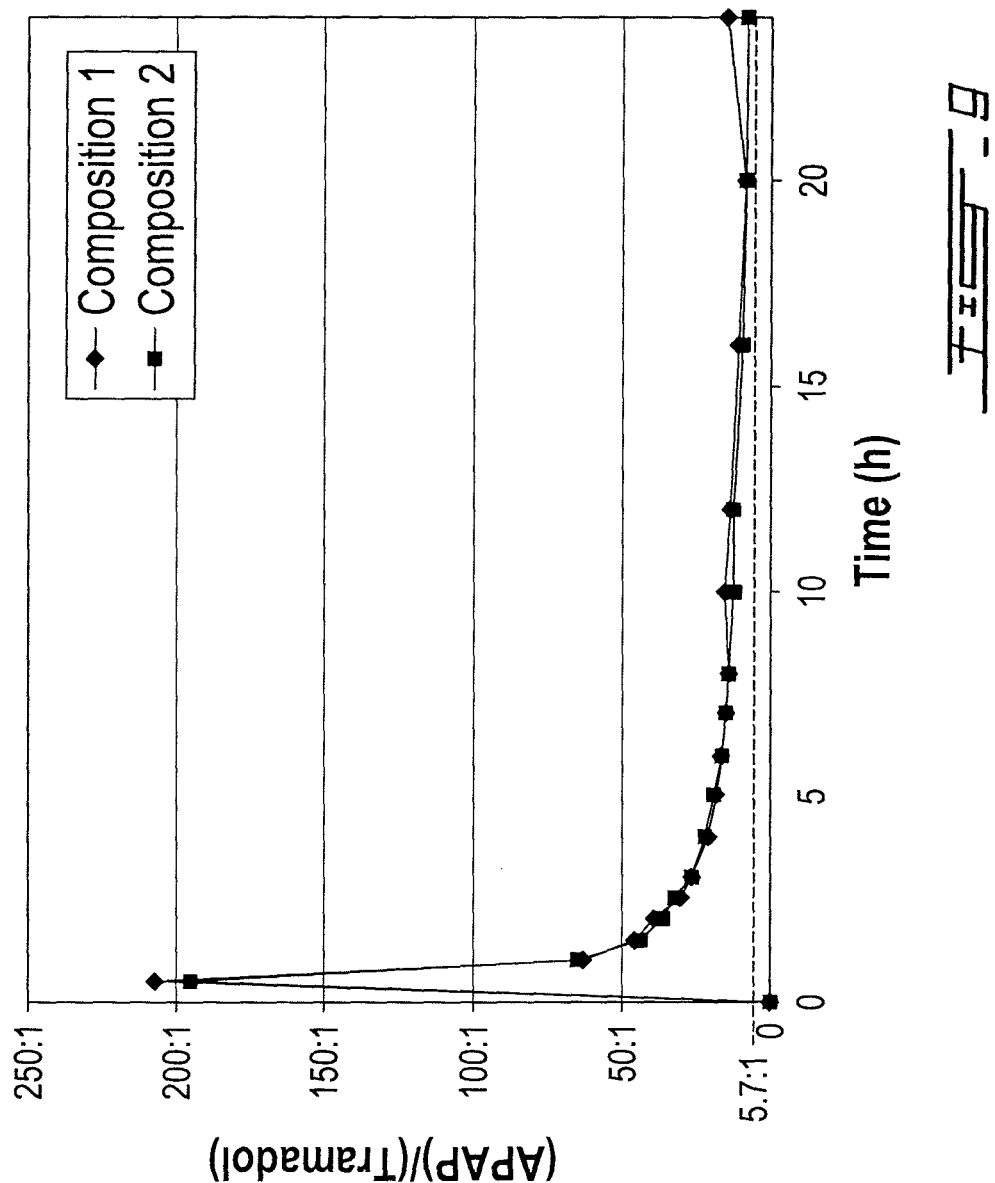
FIG. 9 is a graph illustrating the ratio by weight of acetaminophen:tramadol in the plasma following administration of Composition 1 (-♦-) or Composition 2 (-■-) as a function of time following administration.

It is understood that under certain conditions, the analgesic properties of acetaminophen and tramadol can be additive (for example, where the weight ratio of acetaminophen to tramadol is less than 5.7:1) whereas under certain circumstances the analgesic properties of acetaminophen and tramadol can be synergistic (for example, based on preclinical data, where the weight ratio of acetaminophen to tramadol is greater than 5.7:1). The compositions of the invention, as discussed in Example 2 and as illustrated in FIG. 4, release acetaminophen and tramadol over 12 hours so that they are capable of interacting synergistically with one another to provide analgesia over the twelve hour period. For example, the compositions of the invention release acetaminophen and tramadol so that the ratio of release is in the range of about 25:1 to about 8:1. Furthermore, as discussed in Example 4 and as shown in FIG. 9, the plasma concentrations of acetaminophen and tramadol are such that the weight ratio of acetaminophen:tramadol is greater than about 6:1 for at least 12 hours.

The bilayer compositions of the invention release acetaminophen and tramadol so that over a twelve hour period of time, the weight ratios of acetaminophen to tramadol released is at least 6:1, is at least 7:1. is at least 8:1, is at least 9:1, or is at least 10:1. It is understood that in certain embodiments, the weight ratio of acetaminophen to tramadol released ranges from about 25:1 when measured within about 30 minutes to 1 hour, and then falls gradually to about 8:1 over 12 hours when measured in vitro in a U.S.P. Type III apparatus. It is understood that in certain embodiments, the weight ratio of acetaminophen to tramadol in plasma ranges from about 200:1 within about 30 minutes to 1 hour after administration and then declines to about 6:1 to 10:1 over 12 hours. As a result, it is contemplated that the amount of acetaminophen released from the bilayer composition is sufficient for the acetaminophen and tramadol to act synergistically with one another over a prolonged period of time so that the bilayer composition can provide rapid pain relief that is believed to be sustainable over 12 hours.

As shown in Example 5, the bilayer compositions of the invention can be broken or otherwise divided into subunits, wherein each subunit has substantially the same release properties as the intact or unbroken solid dosage form from which it was derived. Dosage forms may be bisected, e.g., divided into two substantially equal pieces, or may be divided into other fractional sections, e.g., thirds or fourths. Dosage forms may also be divided into unequal sections, e.g., one-third/two-thirds.

In vitro dissolution profiles of intact and separated bilayer compositions as described herein may be compared using fit factors or other mathematical comparisons. Such fit factors are known to those skilled in the art and are used to predict bioequivalency of different dosage forms. The fit factor $f_1$ represents relative error between two curves, or in other words, the mean relative difference on all measured points. Fit factor $f_1$ is sometimes referred to as the difference factor. The mean relative difference for each sample point should be between about 0 to about 15% for bioequivalence. In some embodiments, compositions and/or formulations may have difference factors between an intact dosage form and subunits of the intact dosage form of less than about 15%, less than about 10%, or less than about 7%. The fit factor $f_2$ is a logarithmic transformation of the mean of squares differences between two curves. Fit factor $f_2$ is sometimes referred to as the similarity factor. The similarity factor should be between about 50 and about 100 for bioequivalence, e.g., between the subunit forms and intact dosage forms. In some embodiments, compositions and/or formulations can have similarity factors between an intact dosage form and the subunits derived from the intact dosage form of at least 50, at least 55, at least 60, at least 65, at least 70, at least 75, at least 80, and at least 85.

Specific sustained dosages can be tailored using the dosage forms by breaking the dosage forms disclosed herein into substantially similar but smaller doses having substantially similar release profiles. For example, smaller doses may be useful for patients lighter in weight and/or for pediatric use. Alternatively, one dosage may be provided, but in a smaller form that may be more acceptable to a patient. For example, a patient may be able to divide a dosage into easier-to-swallow components while still maintaining the release properties of the dosage form. The ability to alter dosage on a patient by patient basis with one dosage form may also be convenient for, e.g., a physician or a pharmacist.

In some embodiments, the dosage forms, e.g., tablets, may be scored. Preferably, scored tablets or un-scored tablets are broken with high breaking accuracy thereby ensuring matching or proportional release profiles from each resultant subdivision. Breaking accuracy may be determined for example, by evaluating the mass uniformity of separated, e.g., bisected, parts of the same tablet. The mass uniformity of a tablet may be determined in terms of relative standard deviation (RSD) from the mean mass of tablet sections using the U.S.P. test limit of uniformity (RSD below 6%). Scoring may have varying depths, e.g., from about 0% (e.g., no scoring) to about 50% of the tablet depth. Each tablet may have one, two, or multiple scores, and/or scoring on one or both sides of the tablet.

In certain embodiments, the acetaminophen can divided between the first and second layers as described in TABLE 2.

TABLE 2

| Percent of Total Acetaminophen of Bilayer Composition Located in First Layer | Percent of Total Acetaminophen of Bilayer Composition Located in Second Layer |
|---|---|
| 10% | 90% |
| 15% | 85% |
| 20% | 80% |
| 25% | 75% |
| 30% | 70% |
| 35% | 65% |
| 40% | 60% |
| 45% | 55% |
| 50% | 50% |
| 55% | 45% |
| 60% | 40% |
| 65% | 35% |
| 70% | 30% |

Similarly, in certain embodiments, the tramadol can divided between the first and second layers as described in TABLE 3.

TABLE 3

| Percent of Total Tramadol of Bilayer Composition Located in First Layer | Percent of Total Tramadol of Bilayer Composition Located in Second Layer |
|---|---|
| 0% | 100% |
| 5% | 95% |
| 10% | 90% |
| 15% | 85% |
| 20% | 80% |
| 25% | 75% |
| 30% | 70% |
| 35% | 65% |
| 40% | 60% |
| 45% | 55% |
| 50% | 50% |

In one embodiment, the first layer (the rapid release portion) comprises about 30-40% of the total acetaminophen content of the bilayer composition, and the second layer (the sustained release portion) comprises 60-70% of the total acetaminophen content of the bilayer composition and 100% of the tramadol of the bilayer composition. In another embodiment, the first layer comprises about 40% of the total acetaminophen content of the bilayer composition, and the second layer comprises 60% of the total acetaminophen content of the bilayer composition and 100% of the tramadol in the bilayer composition. In another embodiment, the first layer comprises about 30% of the total acetaminophen content of the bilayer composition, and the second layer comprises about 70% of the total acetaminophen content of the bilayer composition and 100% of the tramadol in the bilayer composition.

Under certain circumstances, the first layer comprises from about 70% to about 90% w/w of acetaminophen. The second layer comprises from about 40% to about 60% w/w acetaminophen and from about 5% to about 15% w/w of tramadol.

The cross-linked high amylose starch acts as a controlled release excipient. In certain embodiments, the second layer comprises from about 5% w/w to about 30% w/w of cross-linked high amylose starch, and more preferably from about 10% w/w to about 20% w/w of cross-linked high amylose starch. In certain embodiments, the second layer comprises about 5%, 6%, 7%, 8%, 9%, 10%, 11%, 12%, 13%, 14%, 15%, 16%, 17%, 18%, 19%, 20%, 21%, 22%, 23%, 24%, or 25% w/w of cross-linked high amylose starch.

In one embodiment, the cross-linked high amylose starch is cross-linked with phosphorus oxychloride and/or comprises hydroxypropyl side chains. A suitable excipient has been developed by and is available commercially from Labopharm, Inc., Laval, Canada, under the tradename CONTRAMID®. The synthesis of the CONTRAMID® excipient is described, for example, in U.S. Pat. No. 6,607,748, hereby incorporated by reference in its entirety for all purposes. Compositions contemplated herein may include cross-linked high amylose starch together with one or more additional controlled release excipients, for example, hydroxypropylmethylcellulose.

Cross-linking of starch represents a powerful method for modifying starch. Usually, starch granules are cross-linked to increase resistance of the paste to shear or heat. Such chemically cross-linked starches provide a desirable smooth texture and possess viscosity stability throughout processing operations and normal shelf life. In some embodiments, cross-linked high amylose starch as contemplated herein may be gelatinized after cross-linking. In a preferred embodiment, cross-linking high amylose starch may include additional chemical modification (e.g., hydroxypropylation) prior to gelatinization.

The cross-linking of high amylose starch may be realized according to procedures described in the art. For example, cross-linking of amylose can be carried out in the manner described in Mateescu [BIOCHEMIE 60: 535-537 (1978)] by reacting amylose with epichlorohydrin in an alkaline medium. In the same manner, starch can also be cross-linked with a reagent selected from the group consisting of epichlorohydrin, adipic acid anhydride, sodium trimetaphosphate and phosphorous oxychloride or other cross-linking agents including, but not limited to, 2,3-dibromopropanol, linear mixed anhydrides of acetic and di- or tribasic carboxylic acids, vinyl sulfone, diepoxides, cyanuric chloride, hexahydro-1,3,5-trisacryloyl-s-triazine, hexamethylene diisocyanate, toluene 2,4-diisocyanate, N,N-methylenebisacrylamide, N,N'-bis (hydroxymethyl) ethyleneurea, mixed carbonic-carboxylic acid anhydrides, imidazolides of carbonic and polybasic carboxylic acids, imidazolium salts of polybasic carboxylic acids, and guanidine derivatives of polycarboxylic acids. The reaction conditions employed will vary with the type and amount of the cross-linking agent that is used, as well as the base concentration, amount and type of starch.

It is contemplated that starches containing more than about 40% w/w amylose can be used to form cross-linked high amylose starch, e.g., pea and wrinkled pea starch, bean starch, hybrids or genetically modified tapioca or potato starch, or any other root, tuber or cereal starch. Preferably, high amylose starch containing about 70% w/w amylose is used as the base material. For example, high amylose starch, Cerestar AmyloGel 03003 (Cerestar U.S.A. Inc.), may be used. In certain formulations, the excipient comprises cross-linked high amylose starch comprising between about 65% and about 75% w/w amylose cross-linked with phosphorus oxychloride.

In certain other embodiments, the second layer optionally comprises hydroxypropylmethylcellulose to enhance the sustained release properties of the second layer. In certain embodiments, the second layer comprises from about 5% w/w to about 20% w/w of hydroxypropylmethylcellulose. In certain embodiments, the second layer comprises 6%, 7%, 8%, 9%, 10%, 11%, 12%, 13%, 14% or 15% w/w hydropropylmethyl cellulose.

In certain embodiments, the first layer optionally further comprises one or more of a granulation agent, a filler, a disintegrant, a lubricant, and a glidant. In addition, in certain embodiments, the second layer optionally further comprises one or more of a granulation agent, a filler, binder, a lubricant, and a glidant.

Exemplary granulation agents for use in the first layer and/or the second layer can be selected from the group consisting of copovidone and starch. Starch, however, is preferred. Exemplary fillers for use in the first layer and/or the second layer can be selected from the group consisting of spray dried lactose, pregelatinized starch, dextrin, maltose and microcrystalline cellulose. However, microcrystalline cellulose is preferred. Exemplary lubricants for use in the first layer and/or the second layer can be selected from the group consisting of sodium stearyl fumarate, magnesium stearate, calcium stearate, stearic acid, hydrogenated vegetable oils or the like. However, sodium stearyl fumarate is preferred. Exemplary glidants for use in the first layer and/or the second layer can be selected from the group consisting colloidal silicon dioxide, talc or the like. However, colloidal silicon dioxide is preferred. Exemplary disintegrants, for use in the first layer, can be selected from the group consisting of crospovidone, sodium starch glycolate, sodium alginate and croscarmelose sodium. However, croscarmelose sodium is preferred. Exemplary binders for use in the second layer can be selected from the group consisting of polyethylene oxide, methylcellulose, hydropropyl cellulose, hydroxyethyl cellulose, polycarbophil and copovidone. However, copovidone is preferred. It is understood that other additives well known to those skilled in the art may of course be included in the bilayer composition according to the invention without departing from the scope and spirit of the present invention.

In one embodiment, the first and second layers have the following compositions. The first layer (rapid release layer) comprises from about 70% to about 90% w/w of acetaminophen, from about 5% to about 15% w/w starch, from about 1 to about 4% w/w microcrystalline cellulose, from about 1% to about 3% w/w croscarmelose sodium, from about 0.5% to about 2% w/w sodium stearyl fumarate, and from about 0.1% to about 1% w/w colloidal silicon dioxide. The second layer (sustained release layer) comprises from about 40% to about 60% w/w acetaminophen, from about 5% to about 15% w/w tramadol, from about 5% to about 10% w/w starch, from about 1% to about 6% w/w microcrystalline cellulose, from about 5% to about 25% w/w cross-linked high amylose starch, from about 5% to about 15% w/w hydroxypropylmethylcellulose, from about 0% to about 5% w/w copovidone, from about 0.5% to about 2% w/w sodium stearyl fumarate, and from about 0.1% to about 1% w/w colloidal silicon dioxide.

It is understood that the bilayer compositions of the invention may take a variety of shapes and forms, for example, tablets, caplets or ovoid, and may be coated or uncoated. However tablets are preferred.

An exemplary formulation protocol for producing the bilayer tablets of the invention is as follows. The composition of the first layer (rapid release layer) is formed by mixing COMPAP®-L (from Mallinckrodt Chemical Inc.) (a mixture of acetaminophen and starch), colloidal silicon dioxide, microcrystalline cellulose, and sodium stearyl fumarate. The composition of the second layer (sustained release layer) is formed by mixing COMPAP®-L, colloidal silicon dioxide, microcrystalline cellulose, Contramid® (Labopharm Inc., Laval, Canada), tramadol HCl, plasdone S-630, hydroxypropylmethylcellulose, and sodium stearyl fumarate. The bilayer tablet is produced using a Piccola™ bilayer tablet press (SMI Inc., NJ, USA) using the compositions for the first and second layers. The bilayer tablets have a preferred hardness in the range of 190 to 250 Newtons.

It is understood that the compositions can be used for treating a mammal, for example, a human, in need of analgesia. The compositions can be used, for example, in the management of acute pain. The method comprises administering one of the compositions described herein, which contains an effective amount of tramadol and acetaminophen. When administered to the mammal, for example, a human, as a single bolus dose that can include, for example, one tablet or multiple tablets, the bilayer composition achieves (i) an effective plasma concentration of acetaminophen within about half an hour after initial administration and lasting at least about twelve hours after initial administration, and (ii) an effective plasma concentration of tramadol for at least about twelve hours after initial administration.

The invention will now be illustrated by means of the following examples which are given for the purpose of illustration only and without any intention to limit the scope of the present invention.

EXAMPLES

Example 1

In this example, two bilayer compositions, referred to as Composition 1 and Composition 2, were created and their in vitro release properties characterized in a U.S.P. Type III Apparatus as described in U.S.P. 30 at 20 dips per minute, at 37±0.5° C., in 250 mL of potassium phosphate monobasic pH 6.8 for one hour, followed by an additional eleven hours after the initial potassium phosphate solution has been removed and replaced with 250 mL of fresh potassium phosphate monobasic pH 6.8.

A first exemplary bilayer composition, referred to as Composition 1, was prepared with the components described in TABLE 4. TABLE 4A describes the formulation of the rapid release layer, TABLE 4B describes the formulation of the sustained release layer, and TABLE 4C describes the amount of each component as a percentage of the intact tablet.

TABLE 4A

| Rapid Release Layer of Composition 1 | | |
|---|---|---|
| Ingredients | Layer (mg) | Layer % |
| Acetaminophen | 260.0 | 84.3 |
| Starch | 28.89 | 9.4 |
| Microcrystalline cellulose | 7.24 | 2.3 |
| Croscarmelose sodium | 6.14 | 2.0 |
| Sodium stearyl fumarate | 4.62 | 1.5 |
| Colloidal silicon dioxide | 1.54 | 0.5 |
| FD&C Yellow 6 | 0.12 | 0.0 |
| Total | 308.55 | 100 |

TABLE 4B

Sustained Release Layer of Composition 1

| Ingredients | Layer (mg) | Layer % |
|---|---|---|
| Acetaminophen | 390.0 | 53.5 |
| Starch | 43.33 | 5.9 |
| Tramadol HCl | 75.0 | 10.3 |
| Microcrystalline cellulose | 17.29 | 2.4 |
| CONTRAMID ® | 145.0 | 19.9 |
| Hydroxypropylmethylcellulose | 43.5 | 6.0 |
| Sodium stearyl fumarate | 10.95 | 1.5 |
| Colloidal silicon dioxide | 3.63 | 0.5 |
| Total | 728.7 | 100 |

TABLE 4C

Percentage of Each Component in the Intact Tablet

| Ingredients | Tablet (mg) | Tablet % |
|---|---|---|
| Acetaminophen | 650.0 | 62.7 |
| Tramadol HCl | 75.0 | 7.2 |
| Starch | 72.22 | 7.0 |
| Microcrystalline cellulose | 24.53 | 2.4 |
| Croscarmellose sodium | 6.14 | 0.6 |
| Sodium stearyl fumarate | 15.57 | 1.5 |
| Colloidal silicon dioxide | 5.17 | 0.5 |
| FD&C Yellow 6 | 0.12 | 0.0 |
| CONTRAMID ® | 145.0 | 14.0 |
| Hydroxypropylmethylcellulose | 43.5 | 4.2 |
| Total | 1037.25 | 100 |

Composition 1 was prepared as follows by mixing the components for each layer and then producing the bilayer tablet using a Piccola™ bilayer tablet press (SMI Inc., NJ, USA). The resulting bilayer tablet had a hardness in the range of 190 to 250 Newtons.

Figure 2:
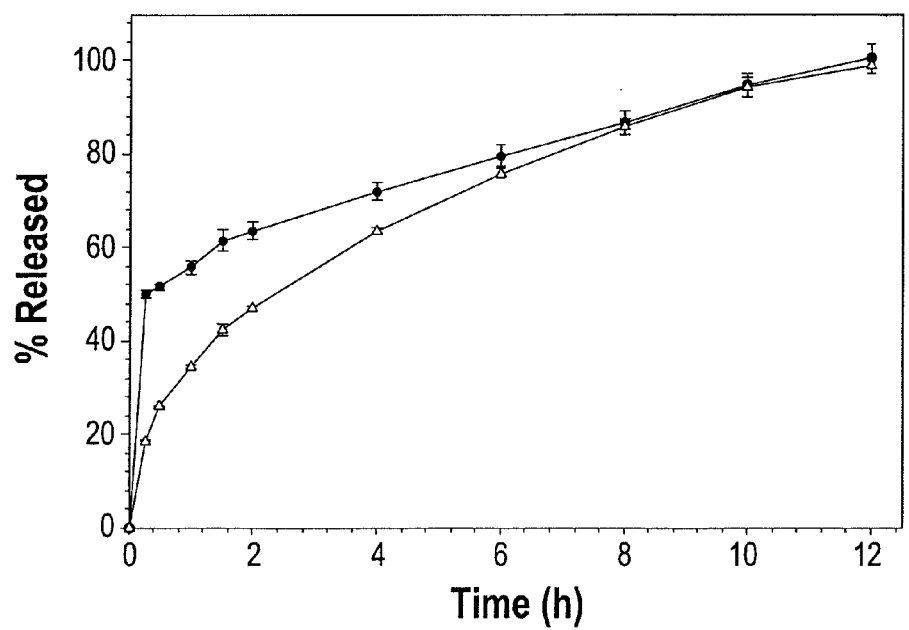
FIG. 2 is a graph illustrating the in vitro dissolution profile of an exemplary intact bilayer composition (Composition 1 of Example 1) showing the release of acetaminophen (●) or tramadol (Δ) over a 12 hour period using a U.S.P. apparatus Type III.

After manufacture, the in vitro release profiles for acetaminophen and tramadol were measured using the U.S.P. (Type III Apparatus) under the conditions noted above. The results are summarized in FIG. 2. Acetaminophen release is shown by filled circles and the tramadol release is shown by open triangles. According to FIG. 2, at least 50% of the acetaminophen was released within the first hour, whereas the remainder of the acetaminophen was released over the remaining eleven hours. Over about the first thirty minutes, the acetaminophen was released with burst release kinetics and thereafter with quasi-zero order release kinetics. Tramadol was released over the entire twelve hour period with first order release kinetics.

A second bilayer composition, referred to as Composition 2, was prepared with the components described in TABLE 5. TABLE 5A describes the formulation of the rapid release layer, TABLE 5B describes the formulation of the sustained release layer of Composition 2, and TABLE 5C describes the amount of each component as a percentage of the intact tablet.

TABLE 5A

Rapid Release Layer of Composition 2

| Ingredients | Layer (mg) | Layer % |
|---|---|---|
| Acetaminophen | 195.0 | 84.4 |
| Starch | 21.66 | 9.4 |
| Microcrystalline cellulose | 6.16 | 2.7 |
| Croscarmellose sodium | 4.62 | 2.0 |
| Sodium stearyl fumarate | 2.31 | 1.0 |
| Colloidal silicon dioxide | 1.16 | 0.5 |
| FD&C Yellow 6 | 0.09 | 0.0 |
| Total | 231.0 | 100 |

TABLE 5B

Sustained Release Layer of Composition 2

| Ingredients | Layer (mg) | Layer % |
|---|---|---|
| Acetaminophen | 455 | 54.2 |
| Starch | 50.55 | 6.0 |
| Tramadol HCl | 75.0 | 8.9 |
| Microcrystalline cellulose | 36.85 | 4.4 |
| CONTRAMID ® | 84.0 | 10.0 |
| Hydroxypropylmethylcellulose | 92.4 | 11.0 |
| Copovidone | 33.6 | 4.0 |
| Sodium stearyl fumarate | 8.4 | 1.0 |
| Colloidal silicon dioxide | 4.2 | 0.5 |
| Total | 840.0 | 100 |

TABLE 5C

Percentage of Each Component in the Intact Tablet

| Ingredients | Tablet (mg) | Tablet % |
|---|---|---|
| Acetaminophen | 650.0 | 60.7 |
| Tramadol HCl | 75.0 | 7.0 |
| Starch | 72.21 | 6.7 |
| Microcrystalline cellulose | 43.01 | 4.0 |
| Croscarmellose sodium | 4.62 | 0.4 |
| Sodium stearyl fumarate | 10.71 | 1.0 |
| Colloidal silicon dioxide | 5.36 | 0.5 |
| FD&C Yellow 6 | 0.09 | 0.01 |
| CONTRAMID ® | 84.0 | 7.8 |
| Hydroxypropylmethylcellulose | 92.4 | 8.6 |
| Copovidone | 33.6 | 3.1 |
| Total | 1071 | 100 |

Figure 3:
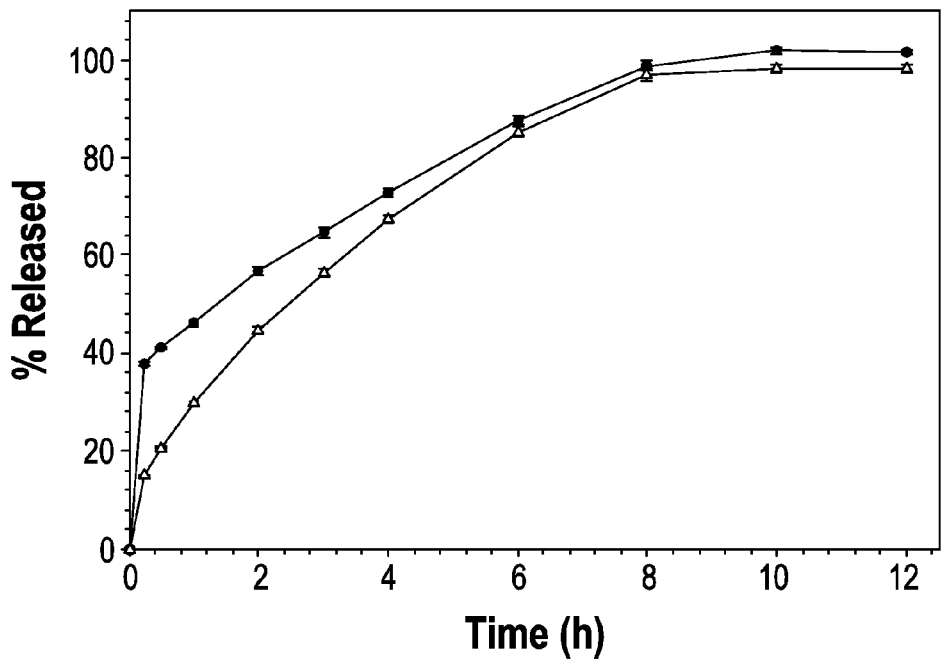
FIG. 3 is a graph illustrating the in vitro dissolution profile of an exemplary intact bilayer composition (Composition 2 of Example 1) showing the release of acetaminophen (●) or tramadol (Δ) over a 12 hour period using a U.S.P. apparatus Type III.

Composition 2 was manufactured as described for Composition 1. The in vitro release profiles for acetaminophen and tramadol were measured as discussed above for Composition 1 and the results are summarized in FIG. 3. Acetaminophen release is shown by filled circles and tramadol release is shown by open triangles. According to FIG. 3, at least 40% of the acetaminophen was released within the first hour, whereas the remainder of the acetaminophen was released over the remaining eleven to eleven and a half hours. Using this composition, the acetaminophen was released with burst release kinetics within about the first thirty minutes followed by quasi-zero order release kinetics for the remainder of time. Tramadol was released over the entire twelve hour period with first order release kinetics.

Example 2

This example shows the relative release of acetaminophen and tramadol from the bilayer compositions as a function of time. In particular, the relative in vitro release kinetics of Composition 2 from Example 1 were studied to determine whether both active ingredients are released in a manner so that they could be capable of acting synergistically with one another.

It is understood that, based on preclinical studies, at weight ratios of acetaminophen to tramadol less than 5.7:1, the therapeutic relief afforded by each active ingredient is believed to be additive. However, at weight ratios of acetaminophen to tramadol greater than 5.7:1, the therapeutic relief afforded by each active ingredient is believed to be synergistic.

FIG. 4 shows the ratio of acetaminophen and tramadol released from Composition 2 over a 12 hour period of time. Within the first 30 minutes, the ratio of acetaminophen to tramadol released was about 25:1. After 12 hours, the ratio fell to about 8:1.

The release kinetics show that acetaminophen is released rapidly suggesting that it is capable of providing rapid analgesia when administered to a mammal. In addition, the release kinetics of both acetaminophen and tramadol suggest that, even after administering a single dose, they are capable of providing sustained relief over the entire twelve hour period.

Example 3

This example describes in vivo plasma concentration levels of tramadol, O-desmethyltramadol (M1), and acetaminophen (APAP) following the administration of Composition 1 to a number of individuals. The results are shown in FIG. 5.

In particular, an open-label, randomized, three-way crossover study was carried out in 17 healthy male and female subjects. The mean concentrations (±SD) of tramadol (see, FIG. 5A), M1 (see, FIG. 5B), and APAP (see, FIG. 5C) were measured over time in plasma obtained from 17 individuals following a single, two-tablet dose of Composition 1 (each tablet contained 75 mg tramadol HCl and 650 mg of acetaminophen) under fasting conditions. The in vivo studies, as shown in FIG. 4, show that acetaminophen has a $T_{max}$ of about 30 minutes to about one hour. Afterwards, the plasma concentration of acetaminophen then declines gradually over the next twenty three hours. Tramadol and M1 have a $T_{max}$ of about four to about six hours. Afterwards, the plasma concentrations of tramadol and M1 decline gradually for the next thirty to thirty two hours.

Figures 6A, 6B, 6C:
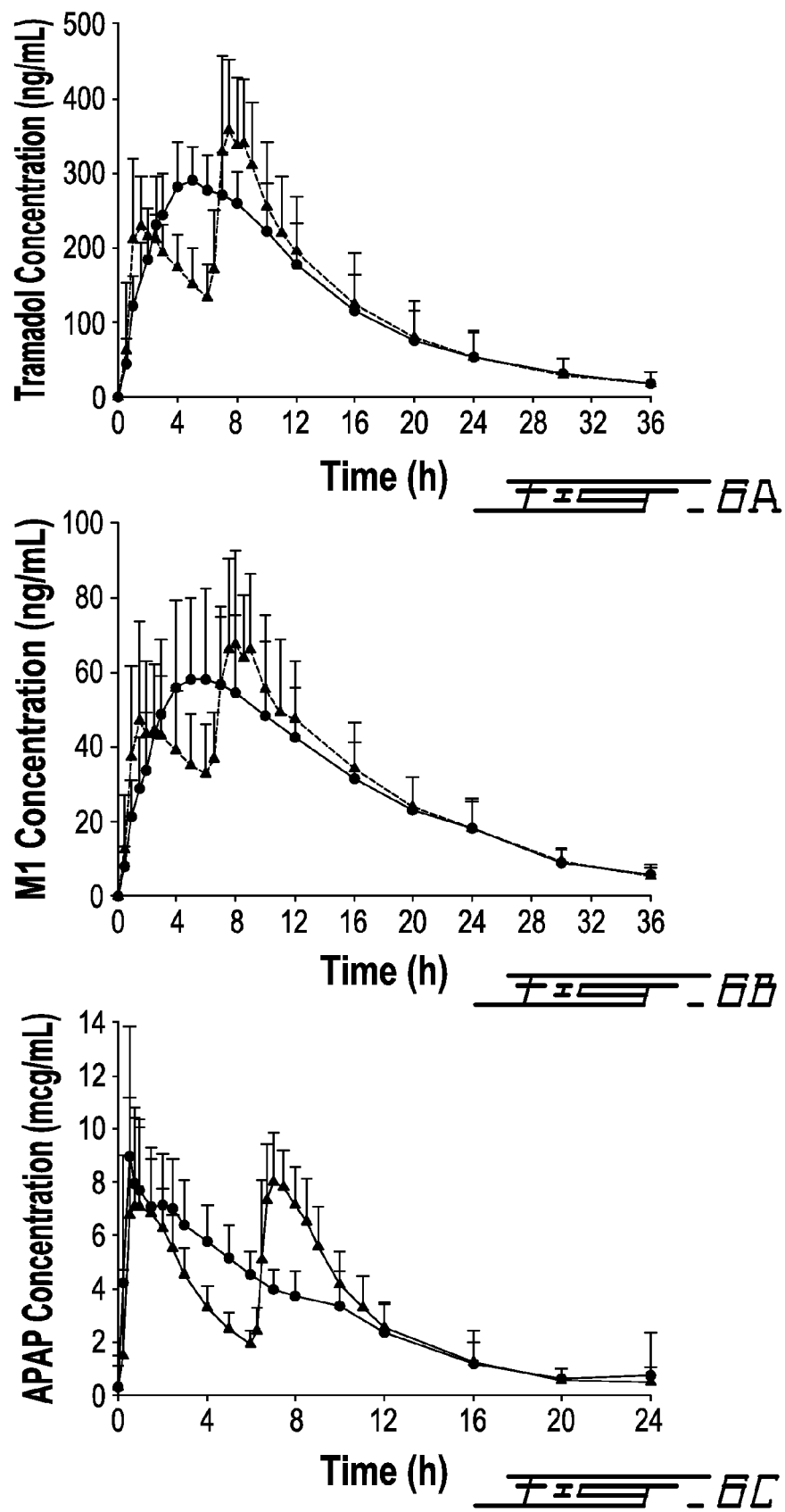
FIGS. 6A-6C are graphs illustrating the in vivo mean plasma concentrations (±SD) of tramadol (FIG. 6A), O-desmethyltramadol (M1)(FIG. 6B), and acetaminophen (APAP) (FIG. 6C) following either (i) a single, two-tablet dose of Composition 1 (each tablet containing 75 mg tramadol and 650 mg of acetaminophen) under fasting conditions (●) or (ii) a two, two-tablet doses of Ultracet® tablets (each tablet containing 37.5 mg tramadol HCl and 325 mg acetaminophen) each dose 6 hours apart (▲), under fasting conditions.

FIG. 6 overlays the plasma concentrations of tramadol (see, FIG. 6A), M1 (see, FIG. 6B) and APAP (see, FIG. 6C) following administration of either (i) a single, two-tablet dose of Composition 1 (each tablet containing 75 mg tramadol HCl and 650 mg of acetaminophen) (filled circles) or (ii) two, two-tablet doses of Ultracet® tablets (each tablet containing 37.5 mg tramadol and 325 mg acetaminophen) administered 6 hours apart (filled triangles), under fasting conditions. The same data showing the plasma concentrations achieved using Composition 1 is plotted in FIGS. 5 and 6. The results demonstrate that it is possible to achieve therapeutically effective plasma concentrations of tramadol and acetaminophen over a twelve hour period using a single dose of Composition 1 as compared to two separate doses of Ultracet® tablets administered 6 hours apart.

Example 4

This example describes the in vivo plasma levels of tramadol, M1, and APAP following a single administration of Composition 2 to a number of individuals. The results are shown in FIG. 7.

The mean concentrations (±SD) of tramadol (see, FIG. 7A), M1 (see, FIG. 7B), and APAP (see, FIG. 7C) were measured over time in plasma obtained from 17 individuals following a single, two-tablet dose of Composition 2 (each tablet contained 75 mg tramadol HCl and 650 mg of acetaminophen) under fasting conditions. The in vivo studies, as shown in FIG. 7, show that acetaminophen has a $T_{max}$ of about 30 minutes to about one hour. Afterwards, the plasma concentration of acetaminophen then declines gradually over the next twenty three hours. Tramadol and M1 have a $T_{max}$ of about four to about six hours. Afterwards, the plasma concentrations of tramadol and M1 decline gradually for the next thirty to thirty two hours.

Figures 8A, 8B, 8C:
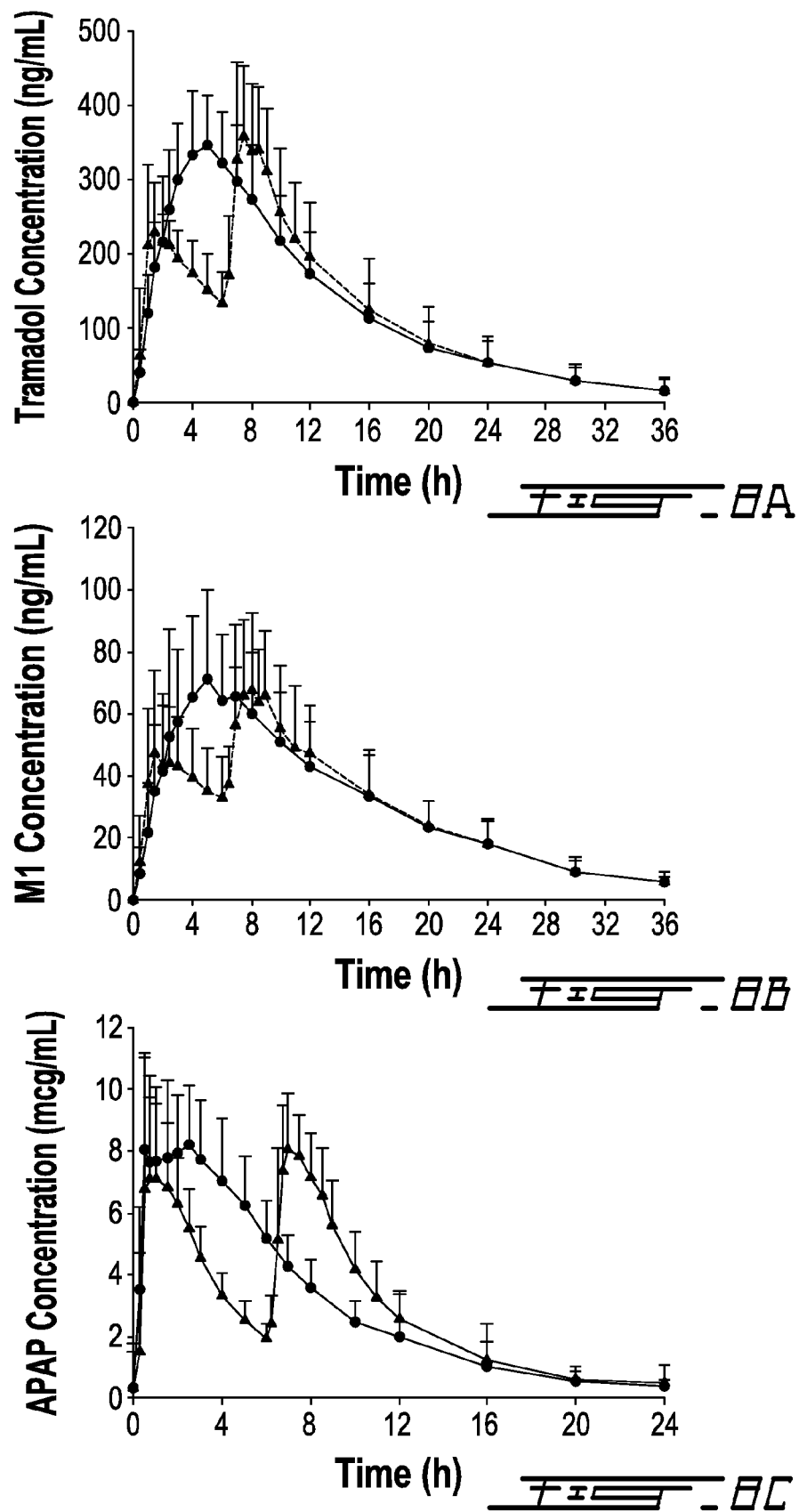
FIGS. 8A-8C are graphs illustrating the in vivo mean plasma concentrations (+SD) of tramadol (FIG. 8A), O-desmethyltramadol (M1)(FIG. 8B), and acetaminophen (APAP) (FIG. 8C) following either (i) a single, two-tablet dose of Composition 2 (each tablet containing 75 mg tramadol and 650 mg of acetaminophen) under fasting conditions (●) or (ii) a two, two-tablet doses of Ultracet® tablets (each tablet containing 37.5 mg tramadol HCl and 325 mg acetaminophen) each dose 6 hours apart (▲), under fasting conditions.

FIG. 8 overlays the plasma concentrations of tramadol (see, FIG. 8A), M1 (see, FIG. 8B) and APAP (see, FIG. 8C) following administration of either (i) a single, two-tablet dose of Composition 2 (each tablet containing 75 mg tramadol HCl and 650 mg of acetaminophen) (filled circles) or (ii) two, two-tablet doses of Ultracet® tablets (each tablet containing 37.5 mg tramadol and 325 mg acetaminophen) administered 6 hours apart (filled triangles), under fasting conditions. The same data showing plasma concentrations achieved using Composition 2 is plotted in FIGS. 7 and 8.

These results, like those in Example 2, demonstrate that it is possible to achieve therapeutically effective plasma concentrations of tramadol and acetaminophen over a twelve hour period using a single dose of Composition 2 as compared to two separate doses of Ultracet® tablets administered six hours apart.

FIG. 9 shows the weight ratio of acetaminophen:tramadol in the plasma of the individuals receiving Composition 1 (see Example 3) and Composition 2 (this Example). The ratios peak at about 200:1 after 30 minutes to 1 hour after administration, after which the ratios decline over the next five to six hours. The weight ratio of acetaminophen to tramadol in the plasma is greater than about 6:1 for at least twelve hours after administration. It appears that both Composition 1 and Composition 2, which have different in vitro release profiles (see FIG. 3), still provide very similar plasma concentration profiles over twenty hours following administration.

Example 5

This example shows that even when the bilayer composition of the invention is subdivided into smaller subunits, the resulting subunits have the same release kinetics as the intact tablets from which they were derived.

Figure 10A:
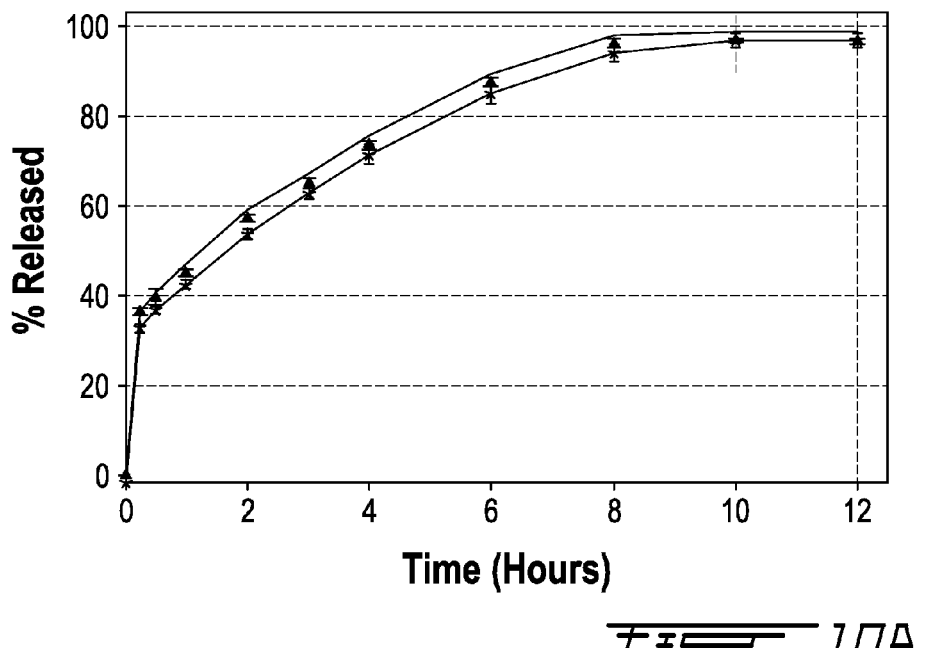
FIGS. 10A-10B are graphs illustrating the release of acetaminophen (FIG. 10A) or tramadol (FIG. 10B) from Composition 2 of Example 1 using a Type III apparatus where the release kinetics of the active ingredient from the intact tablets are denoted by -*- and the release kinetics of active ingredient from half tablets created by breaking intact tablets in half are denoted by -▲-.
Figure 10B:
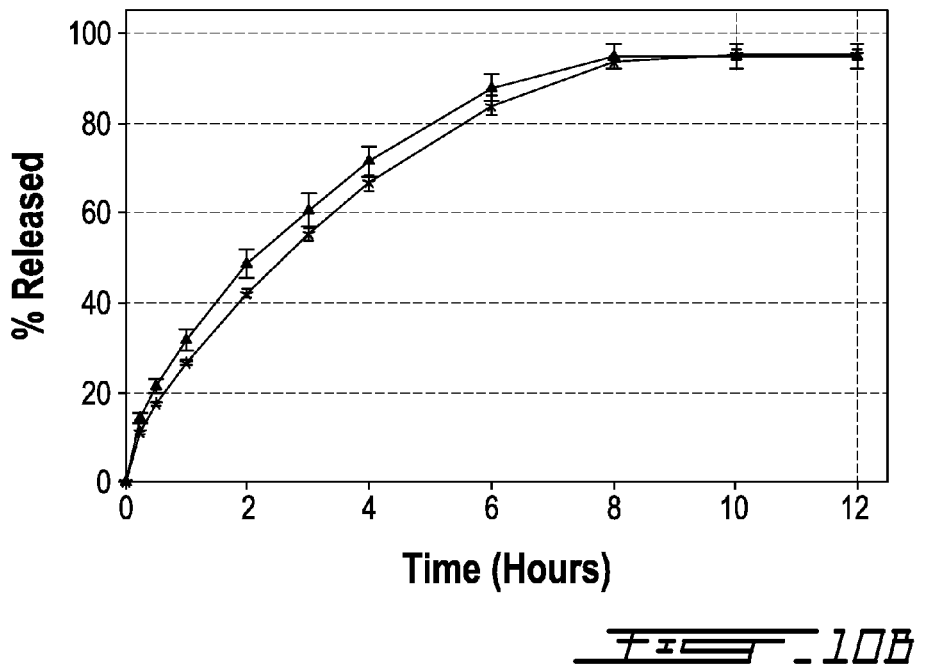

Three bilayer tablets of Composition 2 of Example 1 were cut in half to produce two equal subunits, with each subunit having both the first layer (rapid release layer) and the second layer (the controlled release layer). The kinetics of drug release were measured in the U.S.P. Type III apparatus as described in Example 1 and the release kinetics compared against those achieved from intact tablets. The results are shown in FIG. 10, where FIG. 10A shows the release kinetics of acetaminophen and FIG. 10B shows the release of tramadol. The % release for each half tablet was weight normalized relative to the intact tablet.

The results demonstrate that the kinetics of acetaminophen release (FIG. 10A) was essentially the same for both the intact tablets and the half tablets. Similarly, the kinetics of tramadol release (FIG. 10B) were essentially the same for both the intact tablet and the half tablet. The similarity factors for these curves were at least 50. The difference factors between the intact dosage form and the subunits of the intact dosage form was less than about 15%. These results show that it is possible to bisect the bilayer compositions of the invention into smaller dosage forms without affecting the release kinetics of either active ingredient.

INCORPORATION BY REFERENCE

The entire disclosure of each of the patent and scientific documents referred to herein is incorporated by reference for all purposes.

EQUIVALENTS

Although the present invention has been illustrated by means of preferred embodiments thereof, it is understood that the invention intends to cover broad aspects thereof without departing from the spirit and scope of the invention as defined in the appended claims.

What is claimed is:

1. A bilayer composition for the delivery of tramadol and acetaminophen, the bilayer composition comprising:
   a. a first layer defining a rapid release portion of the composition and comprising a first amount of acetaminophen; and
   b. a second layer defining a sustained release portion of the composition comprising a second amount of acetaminophen, tramadol, and a controlled release excipient selected from the group consisting of cross-linked high amylose starch, and hydroxypropylmethylcellulose, and a mixture thereof, wherein, when tested in a U.S.P. Type III Apparatus at 20 dips per minute at 37° C. in 250 mL of a solution of potassium phosphate monobasic pH 6.8 for one hour, after which the solution is removed and replaced with a fresh 250 mL of potassium phosphate monobasic pH 6.8 for eleven hours, the acetaminophen and tramadol are released with the following kinetics

| Time (hours) | Acetaminophen % release (by weight) | Tramadol % release (by weight) |
| --- | --- | --- |
| 1 | 30-60 | ≤35 |
| 4 | 60-90 | 45-65 |
| 8 | 80-90 | ≤90 |
| 12 | ≥90 | ≥90, | and wherein a single bolus administration of the bilayer composition to a subject achieves (i) an effective plasma concentration of acetaminophen within about half an hour after initial administration, and (ii) effective plasma concentrations of acetaminophen and tramadol over a twelve hour period following initial administration.

2. The composition of claim 1, wherein the second layer comprises both cross-linked high amylose starch and hydroxypropylmethylcellulose.

3. The composition of claim 1, wherein the first layer comprises one or more of a granulation agent, a filler, a disintegrant, a lubricant, and a glidant.

4. The composition of claim 1, wherein the second layer comprises one or more of a granulation agent, a filler, a binder, a lubricant, and a glidant.

5. The composition of claim 1, wherein the second layer comprises from 5% w/w to 30% w/w of cross-linked high amylose starch.

6. The composition of claim 1, wherein (i) the first layer comprises about 10% of the acetaminophen and the second layer comprises about 90% of the acetaminophen, (ii) the first layer comprises about 15% of the acetaminophen and the second layer comprises about 85% of the acetaminophen, (iii) the first layer comprises about 20% of the acetaminophen and the second layer comprises about 80% of the acetaminophen, (iv) the first layer comprises about 25% of the acetaminophen and the second layer comprises about 75% of the acetaminophen, (v) the first layer comprises about 30% of the acetaminophen and the second layer comprises about 70% of the acetaminophen, (vi) the first layer comprises about 35% of the acetaminophen and the second layer comprises about 65% of the acetaminophen, (vii) the first layer comprises about 40% of the acetaminophen and the second layer comprises about 60% of the acetaminophen, (viii) the first layer comprises about 45% of the acetaminophen and the second layer comprises about 55% of the acetaminophen, (ix) the first layer comprises about 50% of the acetaminophen and the second layer comprises about 50% of the acetaminophen, (x) the first layer comprises about 55% of the acetaminophen and the second layer comprises about 45% of the acetaminophen, (xi) the first layer comprises about 60% of the acetaminophen and the second layer comprises about 40% of the acetaminophen, (xii) the first layer comprises about 65% of the acetaminophen and the second layer comprises about 35% of the acetaminophen, or (xiii) the first layer comprises about 70% of the acetaminophen and the second layer comprises about 30 of the acetaminophen.

7. The composition of claim 1, further comprising tramadol in the first layer.

8. The composition of claim 7, wherein (i) the first layer comprises about 50% of the tramadol and the second layer comprises about 50% of the tramadol, (ii) the first layer comprises about 45% of the tramadol and the second layer comprises about 55% of the tramadol, (iii) the first layer comprises about 40% of the tramadol and the second layer comprises about 60% of the tramadol, (iv) the first layer comprises about 35% of the tramadol and the second layer comprises about 65% of the tramadol, (v) the first layer comprises about 30% of the tramadol and the second layer comprises about 70% of the tramadol, (vi) the first layer comprises about 25% of the tramadol and the second layer comprises about 75% of the tramadol, (vii) the first layer comprises about 20% of the tramadol and the second layer comprises about 80% of the tramadol, (viii) the first layer comprises about 15% of the tramadol and the second layer comprises about 85% of the tramadol, (ix) the first layer comprises about 10% of the tramadol and the second layer comprises about 90% of the acetaminophen, (x) the first layer comprises about 5% of the tramadol and the second layer comprises about 95% of the tramadol, or (xi) the first layer comprises about 0% of the tramadol and the second layer comprises about 100% of the tramadol.

9. The composition of claim 1, wherein the first layer comprises from 70% to 90% w/w of acetaminophen, and the second layer comprises from 40% to 60% w/w acetaminophen and from 5% to 15% w/w of tramadol.

10. The composition of claim 1, wherein a solvent accessible surface of the bilayer composition defines a score that permits the composition to be fractured along the score to produce two subunits, wherein the composition and the subunits each have dissolution profiles.

11. The composition of claim 10, wherein at least one of the subunits has substantially the same release kinetics for both the acetaminophen and the tramadol as an intact form of the composition.

12. The composition of claim 11, wherein the composition has a hardness in the range from 190 to 250 Newtons.

13. The composition of claim 10, wherein the dissolution profiles of at least one of the subunits and an intact form of the composition have a similarity factor of at least 50.

14. The composition of claim 13, wherein the composition has a hardness in the range from 190 to 250 Newtons.

15. The composition of claim 1, wherein over a 12 hour period of time the ratio by weight of acetaminophen to tramadol released from the bilayer composition is greater than about 6:1.

16. A bilayer composition for the delivery of tramadol and acetaminophen, the bilayer composition comprising:
   a. a first layer defining a rapid release portion of the composition and comprising acetaminophen; and
   b. a second layer defining a sustained release portion of the composition and comprising acetaminophen, tramadol, and a controlled release excipient selected from the group consisting of cross-linked high amylose starch, hydroxypropylmethylcellulose, and a mixture thereof,
   wherein, the bilayer composition, when administered to a subject in a single bolus, (i) achieves an effective plasma concentration of acetaminophen within about half an hour after initial administration, and (ii) releases the acetaminophen and the tramadol so that the ratio by weight of acetaminophen: tramadol in the plasma of the subject is at least 6:1 for at least 12 hours after administration to the subject.

17. A bilayer composition for the delivery of tramadol and acetaminophen, the bilayer composition comprising:
   a. a first layer defining a rapid release portion of the composition and comprising from 70% to 90% w/w of acetaminophen, from 5% to 15% w/w starch, from 1% to 4% w/w microcrystalline cellulose, from 1% to about 3% w/w croscarmelose sodium, from 0.5% to 2% w/w sodium stearyl fumarate, and from 0.1% to 1% w/w colloidal silicon dioxide; and
   b. a second layer adjacent the first layer and defining a sustained release portion of the composition and comprising from 40% to 60% w/w acetaminophen, from 5% to 15% w/w of tramadol, from 5% to 25% w/w cross-linked high amylose starch, from 5% to 10% w/w starch, from 1% to 6% w/w microcrystalline cellulose, from 5% to 15% w/w hydroxypropylmethyl cellulose, from 0% to 5% w/w copovidone, from 0.5% to 2% w/w sodium stearyl fumarate, and from 0.1% to 1% w/w colloidal silicone dioxide,
   wherein a single bolus administration of the bilayer composition to a subject achieves an effective plasma concentration of acetaminophen within half an hour after initial administration.

18. A method of treating a mammal in need of analgesia, the method comprising administering to the mammal the composition of claim 1 so as to provide analgesia for at least twelve hours.

19. A method of treating a mammal in need of analgesia, the method comprising administering to the mammal the composition of claim 16 so as to provide analgesia for at least twelve hours.

20. A method of treating a mammal in need of analgesia, the method comprising administering to the mammal the composition of claim 17 so as to provide analgesia for at least twelve hours.

* * * * *

UNITED STATES PATENT AND TRADEMARK OFFICE
CERTIFICATE OF CORRECTION

PATENT NO. : 8,895,066 B2  
APPLICATION NO. : 12/252117  
DATED : November 25, 2014  
INVENTOR(S) : Bichara et al.

Page 1 of 1

It is certified that error appears in the above-identified patent and that said Letters Patent is hereby corrected as shown below:

In the Claims

At column 16, line 26, delete "about 30 of acetaminophen" and insert --about 30% of acetaminophen--.

Signed and Sealed this
Second Day of June, 2015

Michelle K. Lee
*Director of the United States Patent and Trademark Office*